(12) United States Patent
Kaila

(10) Patent No.: US 10,751,246 B2
(45) Date of Patent: Aug. 25, 2020

(54) ACOUSTIC SHOCK WAVE THERAPEUTIC METHODS

(71) Applicant: Sanjeev Kaila, Atlanta, GA (US)

(72) Inventor: Sanjeev Kaila, Atlanta, GA (US)

( * ) Notice: Subject to any disclaimer, the term of this patent is extended or adjusted under 35 U.S.C. 154(b) by 332 days.

(21) Appl. No.: 15/854,501

(22) Filed: Dec. 26, 2017

(65) Prior Publication Data

US 2019/0192377 A1 Jun. 27, 2019

(51) Int. Cl.
*A61H 23/00* (2006.01)
*A61B 17/22* (2006.01)
*A61B 17/225* (2006.01)
*A61B 18/00* (2006.01)
*A61L 27/36* (2006.01)
*A61B 17/00* (2006.01)

(52) U.S. Cl.
CPC ..... *A61H 23/008* (2013.01); *A61B 17/22004* (2013.01); *A61B 17/225* (2013.01); *A61B 18/00* (2013.01); *A61B 2017/00752* (2013.01); *A61B 2017/00969* (2013.01); *A61L 27/3604* (2013.01)

(58) Field of Classification Search
CPC .......... A61H 23/008; A61H 2201/1207; A61H 2201/1654; A61H 2205/02; A61H 2205/086; A61H 2205/082; A61B 18/00; A61B 17/22004; A61B 17/225; A61B 2017/00752; A61B 2017/00969; A61L 27/3604; A61N 2007/0034; A61N 7/00
See application file for complete search history.

(56) References Cited

U.S. PATENT DOCUMENTS

| 7,470,240 | B2 | 12/2008 | Schultheiss et al. |
| 7,507,213 | B2 * | 3/2009 | Schultheiss .......... A61H 23/008 600/437 |
| 7,544,171 | B2 * | 6/2009 | Schaden .............. A61H 23/008 600/427 |
| 7,841,995 | B2 | 11/2010 | Schultheiss et al. |
| 7,883,482 | B2 | 2/2011 | Schultheiss et al. |
| 7,905,845 | B2 | 3/2011 | Warlick et al. |
| 8,257,282 | B2 | 9/2012 | Uebelacker et al. |
| 8,298,162 | B2 | 10/2012 | Del Giglio |

(Continued)

FOREIGN PATENT DOCUMENTS

| CA | 2975931 | 8/2016 |
| CN | 101850132 | 10/2010 |

(Continued)

*Primary Examiner* — Sanjay Cattungal
(74) *Attorney, Agent, or Firm* — David L. King

(57) ABSTRACT

A method of conditioning a soft tissue region or site of a patient prior to, during or after a fat grafting procedure, or any combination of these, has the steps of: activating an ultrasonic or acoustic shock wave generator or source to emit ultrasonic or acoustic shock waves; subjecting the soft tissue region or site to ultrasonic or acoustic shock waves stimulating the said soft tissue; wherein the emitted waves are focused or unfocused low energy acoustic shock waves or ultrasonic waves and wherein the soft tissue region or site underlies the patient's skin. The soft tissue region or site is one of a buttock, a breast or a scalp. The method of conditioning a soft tissue region or site further has the step of: treating the soft tissue region or site after conditioning and implanting or injecting viable fat cells in a fat grafting procedure.

18 Claims, 15 Drawing Sheets

(56) References Cited

U.S. PATENT DOCUMENTS

| | | | |
|---|---|---|---|
| 8,535,249 B2 | 9/2013 | Uebelacker et al. | |
| 9,506,035 B2 | 11/2016 | Williams et al. | |
| 9,636,516 B2 | 5/2017 | Schwartz | |
| 9,713,731 B2 | 7/2017 | Slayton et al. | |
| 2002/0055731 A1* | 5/2002 | Atala | A61K 41/0028 604/522 |
| 2006/0100550 A1* | 5/2006 | Schultheiss | A61B 17/22004 601/2 |
| 2006/0293708 A1* | 12/2006 | Voss | A61B 17/22004 606/201 |
| 2006/0293725 A1 | 12/2006 | Rubinsky et al. | |
| 2007/0299539 A1* | 12/2007 | Othman | C12N 5/00 623/23.72 |
| 2017/0128496 A1 | 5/2017 | Williams et al. | |
| 2017/0209708 A1 | 7/2017 | Schwarz | |

FOREIGN PATENT DOCUMENTS

| | | |
|---|---|---|
| EP | 1690929 | 8/2006 |
| JP | 2009124982 | 6/2009 |
| KR | 20100025658 | 3/2010 |
| WO | 03084468 | 10/2003 |
| WO | 2007009981 | 1/2007 |
| WO | 2016183307 | 11/2016 |

\* cited by examiner

ACOUSTIC SHOCK WAVE THERAPEUTIC METHODS

TECHNICAL FIELD

The present invention relates to an improved method of fat tissue grafting that increases cell survival and reduces necrosis of the fat cells after implantation by a unique pre-treatment of a fat recipient site utilizing acoustic shock waves.

BACKGROUND OF THE INVENTION

Fat grafting is a very common plastic surgery procedure that involves suctioning fat from one portion of the body, processing that fat and reinjecting the healthy fat into a new tissue bed. A problem with fat grafting is that there are variable survival results from 50-90% that have been reported in literature.

All fat grafting involves two primary and separate procedures. The first is harvesting the fat cells. There are numerous ways to recover fat cells and the most preferred techniques involve recovering fat cells from the patient desiring a fat graft from a fat cell rich donor site. This fat cell recovery often involves liposuction. Once recovered, the fat cells are processed by removing undesirable lipids, anesthetics and medical fluids from the fat with a goal of obtaining healthy fat cells devoid of other tissue. The yield of viable cells after a fat graft procedure can be no greater than the material being injected.

In fat grafting, the surgeon typically over injects the amount of fat cells to allow for necrosis (cell death) that occurs. For the fat cells to survive, a good vascularization of blood supply must be established at the recipient site receiving the fat graft. The advantage of fat grafting to breast or buttock areas for augmentation or scalp regions for hair growth is that it is 100 percent natural. The disadvantage is the two-step process of recovery and then implantation is considered more expensive than a synthetic implant procedure for breast implant, for example. Accordingly, the ability to insure successful and reliable results with the fat grafting technique needs to be established to justify this approach.

It is therefore an object of the present invention to provide an efficient and reliable technique that guarantees the best outcome with a high percentage of viable cell survival.

The present invention employs newly discovered information and refinements in the use of acoustic shock waves to treat patients to enhance successful fat grafting. It is therefore an object of the present invention to provide an efficient and reliable technique that guarantees the best outcome with a high percentage of viable cell survival.

In U.S. Pat. No. 7,470,240 B2, entitled "Pressure Pulse/Shock Wave Therapy Methods And An Apparatus For Conducting The Therapeutic Methods", is disclosed a novel use of unfocused shock waves in a low energy range to stimulate a cellular substance. From this patent a family of treatment patents evolved. The list includes U.S. Pat. Nos. 7,841,995; 7,883,482; 7,905,845 all divisional applications; and U.S. Pat. No. 7,507,213 entitled "Pressure Pulse/Shock Wave Therapy Methods For Organs"; U.S. Pat. No. 7,544,171 B2 entitled "Methods for Promoting Nerve Regeneration and Neuronal Growth and Elongation"; all teaching a new useful way to deliver acoustic shock waves to achieve a healing response. Each of these patents are incorporated herein by reference in their entirety.

In addition, the present invention has recently received U.S. Pat. Nos. 8,257,282 and 8,535,249 for the device to perform these methods by delivering low energy unfocused acoustic shock waves to the cellular tissue being treated. None of these earlier patents provided any guidance on the use of low energy acoustic shock waves on otherwise healthy soft tissue, all deal with the correction of an abnormality or defect or an injury requiring a healing repair. In fact, in the case of treating cellulite, the objective was to destroy fat cells with high energy acoustic waves or even ultrasonic waves that generated cell rupturing shearing forces and heat. In fact, unfocused low energy shock waves had little effect on damaging fat cells to reduce conditions of cellulitis.

While this large volume of research has been rewarded by the granting of numerous patents, much new work has been evolving as the understanding of the technology is being applied. It is in this latest work that some, heretofore, unknown improvements and refinements have been discovered that were hidden from and unappreciated by scientists in this field.

SUMMARY OF THE INVENTION

A method of conditioning a soft tissue region or site of a patient prior to a fat grafting procedure or as part of the fat grafting procedure or after a fat grafting procedure, or any combination of conditioning prior to, during or after a fat grafting procedure, has the steps of: activating sonic waves of either an ultrasonic wave generator or source or an acoustic shock wave generator or source to emit ultrasonic or acoustic shock waves; subjecting the soft tissue region or site to either ultrasonic or acoustic shock waves stimulating the said soft tissue; wherein the emitted ultrasonic or acoustic shock waves are focused or unfocused low energy acoustic shock waves or ultrasonic waves and wherein the soft tissue region or site underlies the patient's skin. The soft tissue region or site is one of a buttock, a breast or a scalp. The method of conditioning a soft tissue region or site further has the step of: taking the soft tissue region or site after conditioning and implanting or injecting viable fat cells in a fat grafting procedure; or having the conditioning as part of the fat grafting procedure with the step of implanting or injecting the viable fat cells, after the fat grafting procedure or any combination of conditioning either prior to, during or after the fat grafting procedure.

The method of conditioning a soft tissue region or site further can have the step of: subjecting the soft tissue region or site prior to receiving or after the fat grafting procedure and further may optionally have the step of verifying or measuring a survival rate of the fat cells after a period of several weeks after the fat graft procedure. The method of conditioning a soft tissue region or site further may also have the step of: repeating one or more times the step of subjecting the soft tissue region or target site to ultrasonic or acoustic shock waves after a period of time after the fat grafting procedure to maintain tissue stimulation.

Preferably, the conditioning employs acoustic shock waves wherein the shock wave generator is acoustically coupled to the patient's skin using a coupling gel or liquid. The conditioning of the soft tissue site causes a release of nitric oxide. The conditioning of the soft tissue site also causes a release of growth factors including, but not limited to VGEF. The conditioning of the soft tissue further causes new blood vessels to be created increasing vascularization. The method of conditioning a soft tissue region or site can be repeated one or more times prior to a fat grafting procedure.

Ideally, the emitted acoustic shock waves are low energy soft waves wherein the low energy soft waves have an energy density of 0.2 mJ/mm². The soft tissue region or site receives between 2000 and 6000 acoustic shock waves per treatment.

Definitions

A "curved emitter" is an emitter having a curved reflecting (or focusing) or emitting surface and includes, but is not limited to, emitters having ellipsoidal, parabolic, quasi parabolic (general paraboloid) or spherical reflector/reflecting or emitting elements. Curved emitters having a curved reflecting or focusing element generally produce waves having focused wave fronts, while curved emitters having a curved emitting surfaces generally produce wave having divergent wave fronts.

"Divergent waves" in the context of the present invention are all waves which are not focused and are not plane or nearly plane. Divergent waves also include waves which only seem to have a focus or source from which the waves are transmitted. The wave fronts of divergent waves have divergent characteristics. Divergent waves can be created in many different ways, for example: A focused wave will become divergent once it has passed through the focal point. Spherical waves are also included in this definition of divergent waves and have wave fronts with divergent characteristics.

"extracorporeal" occurring or based outside the living body.

A "generalized paraboloid" according to the present invention is also a three-dimensional bowl. In two dimensions (in Cartesian coordinates, x and y) the formula $y^n=2px$ [with n being $\neq 2$, but being greater than about 1.2 and smaller than 2, or greater than 2 but smaller than about 2.8]. In a generalized paraboloid, the characteristics of the wave fronts created by electrodes located within the generalized paraboloid may be corrected by the selection of (p (−z,+z)), with z being a measure for the burn down of an electrode, and n, so that phenomena including, but not limited to, burn down of the tip of an electrode (−z,+z) and/or disturbances caused by diffraction at the aperture of the paraboloid are compensated for.

A "paraboloid" according to the present invention is a three-dimensional reflecting bowl. In two dimensions (in Cartesian coordinates, x and y) the formula $y^2=2px$, wherein p/2 is the distance of the focal point of the paraboloid from its apex, defines the paraboloid. Rotation of the two-dimensional figure defined by this formula around its longitudinal axis generates a de facto paraboloid.

"Plane waves" are sometimes also called flat or even waves. Their wave fronts have plane characteristics (also called even or parallel characteristics). The amplitude in a wave front is constant and the "curvature" is flat (that is why these waves are sometimes called flat waves). Plane waves do not have a focus to which their fronts move (focused) or from which the fronts are emitted (divergent). "Nearly plane waves" also do not have a focus to which their fronts move (focused) or from which the fronts are emitted (divergent). The amplitude of their wave fronts (having "nearly plane" characteristics) is approximating the constancy of plain waves. "Nearly plane" waves can be emitted by generators having pressure pulse/shock wave generating elements with flat emitters or curved emitters. Curved emitters may comprise a generalized paraboloid that allows waves having nearly plane characteristics to be emitted.

A "pressure pulse" according to the present invention is an acoustic pulse which includes several cycles of positive and negative pressure. The amplitude of the positive part of such a cycle should be above about 0.1 MPa and its time duration is from below a microsecond to about a second. Rise times of the positive part of the first pressure cycle may be in the range of nano-seconds (ns) up to some milli-seconds (ms). Very fast pressure pulses are called shock waves. Shock waves used in medical applications do have amplitudes above 0.1 MPa and rise times of the amplitude are below 100 ns. The duration of a shock wave is typically below 1-3 micro-seconds (µs) for the positive part of a cycle and typically above some micro-seconds for the negative part of a cycle.

Waves/wave fronts described as being "focused" or "having focusing characteristics" means in the context of the present invention that the respective waves or wave fronts are traveling and increase their amplitude in direction of the focal point. Per definition the energy of the wave will be at a maximum in the focal point or, if there is a focal shift in this point, the energy is at a maximum near the geometrical focal point. Both the maximum energy and the maximal pressure amplitude may be used to define the focal point.

BRIEF DESCRIPTION OF THE DRAWINGS

The invention will be described by way of example and with reference to the accompanying drawings in which.

DETAILED DESCRIPTION OF THE INVENTION

Figure 1A:
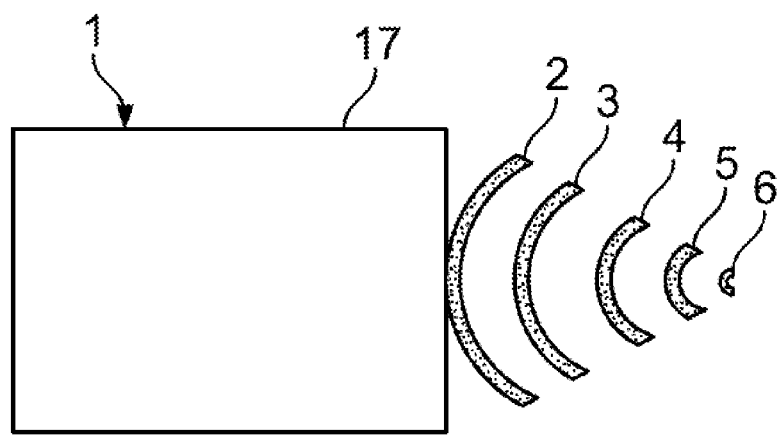
FIG. 1a is a simplified depiction of a pressure pulse/shock wave (PP/SW) generator with focusing wave characteristics.

The present methodology can use sonic waves of an ultrasonic wave form or an acoustic shock wave form. While the ultrasonic wave form is an alternative, it is believed less efficient than acoustic shock waves. The following detailed description of the present invention focused with a more detailed explanation of the preferred acoustic shock waves. It is understood however, that the use of the alternative sonic waves is also being claimed as an alternative wave form for the procedure being claimed herein.

In the Extracorporeal Shock wave method of treating a patient at a target site on the anatomy, the patient is placed in a convenient orientation to permit the source of the emitted waves to most directly send the waves to the target site to initiate shock wave stimulation of the target area. Assuming the target area is within a projected area of the wave transmission, a single transmission dosage of wave energy may be used. The transmission dosage can be from a few seconds to 20 minutes or more dependent on the condition. Preferably the waves are generated from an unfocused or focused source. The unfocused waves can be divergent or near planar and having a low-pressure amplitude and density in the range of 0.00001 $mJ/mm^2$ to 1.0 $mJ/mm^2$ or less, most typically below 0.2 $mJ/mm^2$. The focused source preferably can use a diffusing lens or have a far-sight focus to minimize if not eliminate having the localized focus point within the tissue. Preferably the focused shock waves are used at a similarly effective low energy transmission or alternatively can be at higher energy but wherein the tissue target site is disposed pre-convergence inward of the geometric focal point of the emitted wave transmission.

These shock wave energy transmissions are effective in stimulating a cellular response and can be accomplished without creating the cavitation bubbles in the tissue of the target site. This effectively insures the patient does not have to experience the sensation of pain so common in the higher energy focused wave forms having a focal point at or within the targeted treatment site.

Accordingly, unless for other reasons such as a trauma or immediate post-operative shock wave therapy no localized or general anesthesia is required.

If the target site is within the body it may be such that the patient or the generating source must be reoriented relative to the site and a second, third or more treatment dosage can be administered. The fact that the dosage is at a low energy the common problem of localized hemorrhaging is reduced making it more practical to administer multiple dosages of waves from various orientations to further optimize the treatment and cellular stimulation of the target site. Heretofore focused high energy multiple treatments induced pain and discomfort to the patient. The use of low energy focused or un-focused waves at the target site enables multiple sequential treatments. Alternatively, the wave source generators may be deployed in an array wherein the subject patient is effectively enveloped or surrounded by a plurality of low energy wave source generators which can be simultaneously bombarding the target site from multiple directions.

The goal in such treatments is to provide 2000 to 6000 acoustic shock waves at a voltage of 14 kV to 28 kV across a spark gap generator in a single treatment preferably or one or more adjuvant treatments by targeting the site impinging the emitted waves on the target.

The present method does not rely on precise site location per se. The physician's general understanding of the anatomy of the patient should be sufficient to locate the target site to be treated. The treated area can withstand a far greater number of shock waves based on the selected energy level being emitted. For example, at very low energy levels the stimulation exposure can be provided over prolonged periods as much as 20 minutes if so desired. At higher energy levels the treatment duration can be shortened to less than a minute, less than a second if so desired. The limiting factor in the selected treatment dosage is avoidance or minimization of cell hemorrhaging and other kinds of damage to the cells or tissue while still providing a stimulating cellular release or activation of VEGF and other growth factors.

A key advantage of the present inventive methodology is that it is complimentary to conventional medical procedures. In the case of any post-operative surgical procedure the surgical area of the patient can be post operatively bombarded with these low energy waves to stimulate cellular release of healing agents and growth factors. This will dramatically reduce the healing process and in the case of fat grafting will accelerate the creation of new blood cells to allow the fat cells to survive. Most preferably such patients may be provided more than one such ESWT treatment with an intervening dwell time for cellular relaxation prior to secondary and tertiary treatments.

The underlying principle of these shock wave therapy methods is to stimulate the body's own natural healing capability. This is accomplished by deploying shock waves to stimulate strong cells in the tissue to activate a variety of responses. The acoustic shock waves transmit or trigger what appears to be a cellular communication throughout the entire anatomical structure, this activates a generalized cellular response at the treatment site, in particular, but more interestingly a systemic response in areas more removed from the wave form pattern. This is believed to be one of the reasons molecular stimulation can be conducted at threshold energies heretofore believed to be well below those commonly accepted as required. Accordingly, not only can the energy intensity be reduced but also the number of applied shock wave impulses can be lowered from several thousand to as few as one or more pulses and still yield a beneficial stimulating response.

The biological model motivated the design of sources with low pressure amplitudes and energy densities. First: spherical waves generated between two tips of an electrode; and second: nearly even waves generated by generated by generalized parabolic reflectors. Third: divergent shock front characteristics are generated by an ellipsoid behind F2. Unfocused sources are preferably designed for extended two dimensional areas/volumes like skin. The unfocused sources can provide a divergent wave pattern or a nearly planar wave pattern and can be used in isolation or in combination with focused wave patterns yielding to an improved therapeutic treatment capability that is non-invasive with few if any disadvantageous contraindications. Alternatively, a focused wave emitting treatment may be used wherein the focal point extends preferably beyond the target treatment site, potentially external to the patient. This results in the reduction of or elimination of a localized intensity zone with associated noticeable pain effect while providing a wide or enlarged treatment volume at a variety of depths more closely associated with high energy focused wave treatment. The utilization of a diffuser type lens or a shifted far-sighted focal point for the ellipsoidal reflector enables the spreading of the wave energy to effectively create a convergent but off target focal point. This insures less tissue trauma while insuring cellular stimulation to enhance the healing process.

This method of treatment has the steps of, locating a treatment site, generating either convergent diffused or far-sighted focused shock waves or unfocused shock waves, of directing these shock waves to the treatment site; and applying a sufficient number of these shock waves to induce activation of one or more growth factor thereby inducing or accelerating healing.

The unfocused shock waves can be of a divergent wave pattern or near planar pattern preferably of a low peak pressure amplitude and density. Typically, the energy density values range as low as 0.000001 mJ/mm$^2$ and having a high end energy density of below 1.0 mJ/mm$^2$, preferably 0.20 mJ/mm$^2$ or less. The peak pressure amplitude of the positive part of the cycle should be above 1.0 and its duration is below 1-3 microseconds.

The treatment depth can vary from the surface to the full depth of the human or animal torso and the treatment site can be defined by a much larger treatment area than the 0.10-3.0 cm$^2$ commonly produced by focused waves. The above methodology is particularly well suited for surface as well as sub-surface soft tissue treatments.

The above methodology is valuable in generation of tissue, vascularization and may be used in combination with stem cell therapies as well as regeneration of tissue and vascularization.

The following invention description first provides a detailed explanation of acoustic shock waves, as illustrated in FIGS. 1a-12. As used herein an acoustic shock wave is an asymmetric wave with an exceptionally rapid peak rise time and slower return time from the peak amplitude. Historically, these acoustic shock waves were first used medically to destroy kidney stones. The wave patterns were directed to a focal point with ah a relatively high energy to blast the concrements into small urinary tract passable fragments.

A whole class of acoustic shock waves for medical treatments were later discovered that employed low energy acoustic shock waves. These low energy acoustic shock waves maintained the asymmetric wave profile, but at much lower energies as described in US2006/0100550 which is incorporated herein in its entirety.

These low energy acoustic shock waves advantageously could stimulate a substance without requiring a focused beam. The advantage of such an unfocused beam was the acoustic wave could be directed to pass through tissue without causing any cell rupturing which would be evidenced by a lack of a hematoma or bruising. This use of unfocused, low energy acoustic shock waves provided an ability to treat a large volume of tissue virtually painlessly.

The use of low energy acoustic shock waves that employ a focused beam has been spurred on as a viable alternative to the unfocused low energy shock waves because the focal point being of a small point of energy has little or a small region of cell damage as the remaining portions of the wave pattern can provide a stimulating effect similar to the unfocused shock waves. Basically, the effect is the same with the users of focused waves achieving the benefits of the unfocused waves, but with a focal point of peak energy in a tiny localised region. So, for purposes of the present invention, the use of "soft waves" those defined by low energy beams will be applicable to both focused and unfocused beams o acoustic shock waves for the present invention.

One last and significant point that the reader must appreciate is that an "acoustic shock wave" is not an "ultrasound wave". Sonic or ultrasound waves are generated with a uniform and symmetrical wave pattern similar to a sinusoidal wave. This type of sonic wave causes a sheer action on tissue as evidenced by a generation of heat within the tissue, for this reason, the use of sonic waves of the ultrasonic type are not considered as efficient in fat cell survivability rates, nonetheless, it is believed it can show an improvement albeit not as reliable as acoustic shock waves particularly after a fat grafting procedure, but could be used prior to fat grafting as a preconditioning step.

The present preferred invention avoids the use of such cell damaging sonic waves, most particularly in the post implantation of fat grafts.

With reference to FIGS. 1a-12, a variety of schematic views of acoustic shock waves are described.

FIG. 1a is a simplified depiction of a pressure pulse/shock wave (PP/SW) generator, such as a shock wave head, showing focusing characteristics of transmitted acoustic pressure pulses. Numeral 1 indicates the position of a generalized pressure pulse generator, which generates the pressure pulse and, via a focusing element, focuses it outside the housing to treat diseases. The affected tissue or organ is generally located in or near the focal point which is located in or near position 6. At position 17 a water cushion or any other kind of exit window for the acoustical energy is located.

Figure 1B:
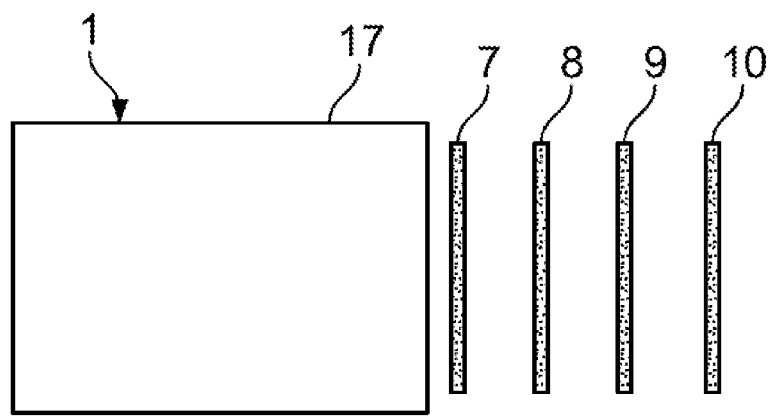
FIG. 1b is a simplified depiction of a pressure pulse/shock wave generator with plane wave characteristics.

FIG. 1b is a simplified depiction of a pressure pulse/shock wave generator, such as a shock wave head, with plane wave characteristics. Numeral 1 indicates the position of a pressure pulse generator according to the present invention, which generates a pressure pulse which is leaving the housing at the position 17, which may be a water cushion or any other kind of exit window. Somewhat even (also referred to herein as "disturbed") wave characteristics can be generated, in case a paraboloid is used as a reflecting element, with a point source (e.g. electrode) that is located in the focal point of the paraboloid. The waves will be transmitted into the patient's body via a coupling media such as, e.g., ultrasound gel or oil and their amplitudes will be attenuated with increasing distance from the exit window 17.

Figure 1C:
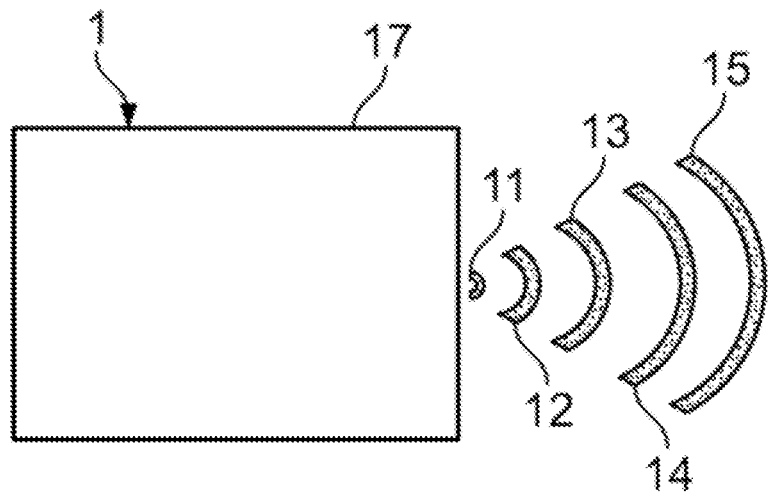
FIG. 1c is a simplified depiction of a pressure pulse/shock wave generator with divergent wave characteristics.

FIG. 1c is a simplified depiction of a pressure pulse shock wave generator (shock wave head) with divergent wave characteristics. The divergent wave fronts may be leaving the exit window 17 at point 11 where the amplitude of the wave front is very high. This point 17 could be regarded as the source point for the pressure pulses. In FIG. 1c the pressure pulse source may be a point source, that is, the pressure pulse may be generated by an electrical discharge of an electrode under water between electrode tips. However, the pressure pulse may also be generated, for example, by an explosion, referred to as a ballistic pressure pulse. The divergent characteristics of the wave front may be a consequence of the mechanical setup shown in FIG. 2b.

Figure 2A:
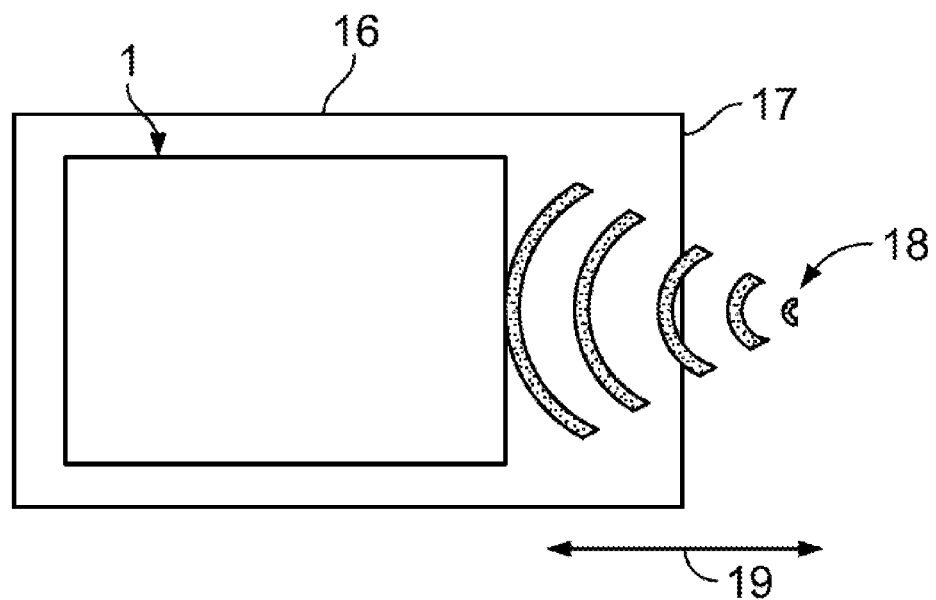
FIG. 2a is a simplified depiction of a pressure pulse/shock wave generator having an adjustable exit window along the pressure wave path. The exit window is shown in a focusing position.

FIG. 2a is a simplified depiction of a pressure pulse/shock wave generator (shock wave head) according to the present invention having an adjustable or exchangeable (collectively referred to herein as "movable") housing around the pressure wave path. The apparatus is shown in a focusing position. FIG. 2a is similar to FIG. 1a but depicts an outer housing (16) in which the acoustical pathway (pressure wave path) is located. In a preferred embodiment, this pathway is defined by especially treated water (for example, temperature controlled, conductivity and gas content adjusted water) and is within a water cushion or within a housing having a permeable membrane, which is acoustically favorable for the transmission of the acoustical pulses. In certain embodiments, a complete outer housing (16) around the pressure pulse/shock wave generator (1) may be adjusted by moving this housing (16) in relation to, e.g., the focusing element in the generator. However, as the person skilled in the art will appreciate, this is only one of many embodiments of the present invention. While the figure shows that the exit window (17) may be adjusted by a movement of the complete housing (16) relative to the focusing element, it is clear that a similar, if not the same, effect can be achieved by only moving the exit window, or, in the case of a water cushion, by filling more water in the volume between the focusing element and the cushion. FIG. 2a shows the situation in which the arrangement transmits focused pressure pulses.

Figure 2B:
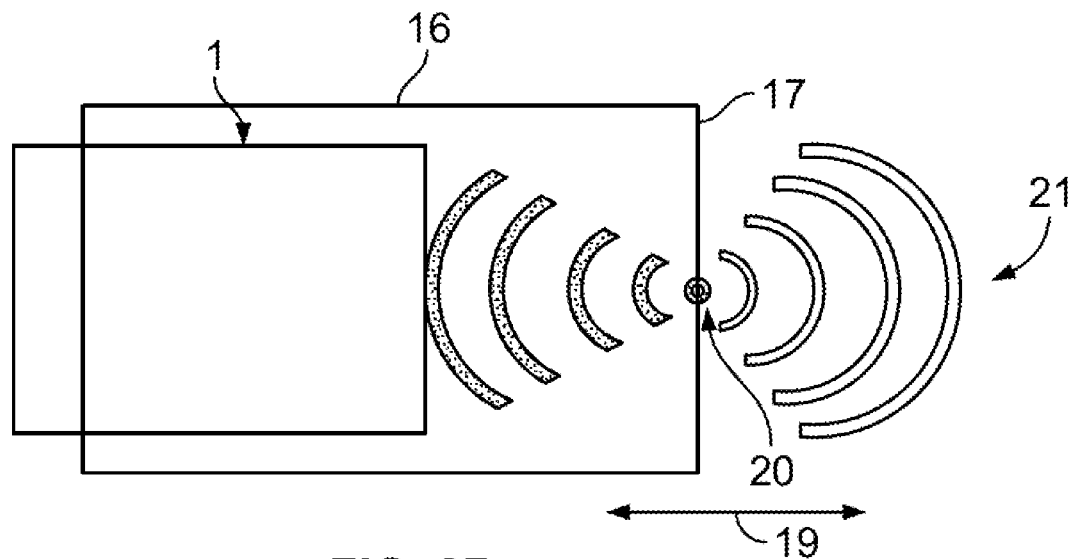
FIG. 2b is a simplified depiction of a pressure pulse/shock wave generator having an exit window along the pressure wave path. The exit window as shown is positioned at the highest energy divergent position.

FIG. 2b is a simplified depiction of the pressure pulse/shock wave generator (shock wave head) having an adjustable or exchangeable housing around the pressure wave path with the exit window 17 being in the highest energy divergent position. The configuration shown in FIG. 2b can, for example, be generated by moving the housing (16) including the exit window (17), or only the exit window (17) of a water cushion, towards the right (as shown in the Figure) to the second focus f2 (20) of the acoustic waves. In a preferred embodiment, the energy at the exit window will be maximal. Behind the focal point, the waves may be moving with divergent characteristics (21).

Figure 2C:
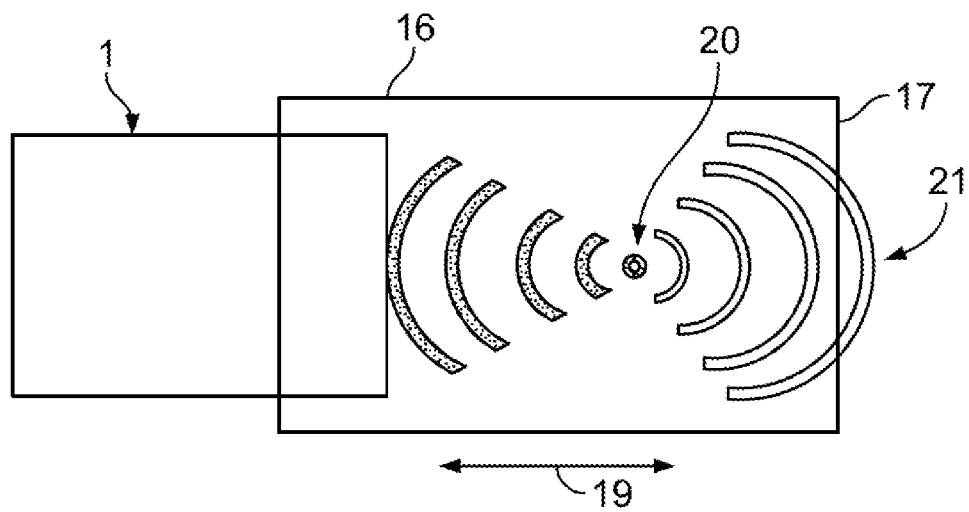
FIG. 2c is a simplified depiction of a pressure pulse/shock wave generator having an exit window along the pressure wave path. The exit window is shown at a low energy divergent position.

FIG. 2c is a simplified depiction of the pressure pulse/shock wave generator (shock wave head) having an adjustable or exchangeable housing around the pressure wave path in a low energy divergent position. The adjustable housing or water cushion is moved or expanded much beyond f2 position (20) so that highly divergent wave fronts with low energy density values are leaving the exit window (17) and may be coupled to a patient's body. Thus, an appropriate adjustment can change the energy density of a wave front without changing its characteristic.

This apparatus may, in certain embodiments, be adjusted/modified/or the complete shock wave head or part of it may be exchanged so that the desired and/or optimal acoustic profile such as one having wave fronts with focused, planar, nearly plane, convergent or divergent characteristics can be chosen.

A change of the wave front characteristics may, for example, be achieved by changing the distance of the exit acoustic window relative to the reflector, by changing the reflector geometry, by introducing certain lenses or by removing elements such as lenses that modify the waves produced by a pressure pulse/shock wave generating element. Exemplary pressure pulse/shock wave sources that can, for example, be exchanged for each other to allow an apparatus to generate waves having different wave front characteristics are described in detail below.

In certain embodiments, the change of the distance of the exit acoustic window can be accomplished by a sliding movement. However, in other embodiments of the present invention, in particular, if mechanical complex arrangements, the movement can be an exchange of mechanical elements.

In one embodiment, mechanical elements that are exchanged to achieve a change in wave front characteristics include the primary pressure pulse generating element, the focusing element, the reflecting element, the housing and the membrane. In another embodiment, the mechanical elements further include a closed fluid volume within the housing in which the pressure pulse is formed and transmitted through the exit window.

In one embodiment, the apparatus of the present invention is used in combination therapy. Here, the characteristics of waves emitted by the apparatus are switched from, for example, focused to divergent or from divergent with lower energy density to divergent with higher energy density. Thus, effects of a pressure pulse treatment can be optimized by using waves having different characteristics and/or energy densities, respectively.

While the above described universal toolbox of the various types of acoustic shock waves and types of shock wave generating heads provides versatility, the person skilled in the art will appreciate that apparatuses that produce low energy or soft acoustic shock waves having, for one example, nearly plane characteristics, are less mechanically demanding and fulfill the requirements of many users.

As the person skilled in the art will also appreciate that embodiments shown in the drawings are independent of the generation principle and thus are valid for not only electrohydraulic shock wave generation but also for, but not limited to, PP/SW generation based on electromagnetic, piezoceramic and ballistic principles. The pressure pulse generators may, in certain embodiments, be equipped with a water cushion that houses water which defines the path of pressure pulse waves that is, through which those waves are transmitted. In a preferred embodiment, a patient is coupled via ultrasound gel or oil to the acoustic exit window (17), which can, for example, be an acoustic transparent membrane, a water cushion, a plastic plate or a metal plate.

Figure 3:
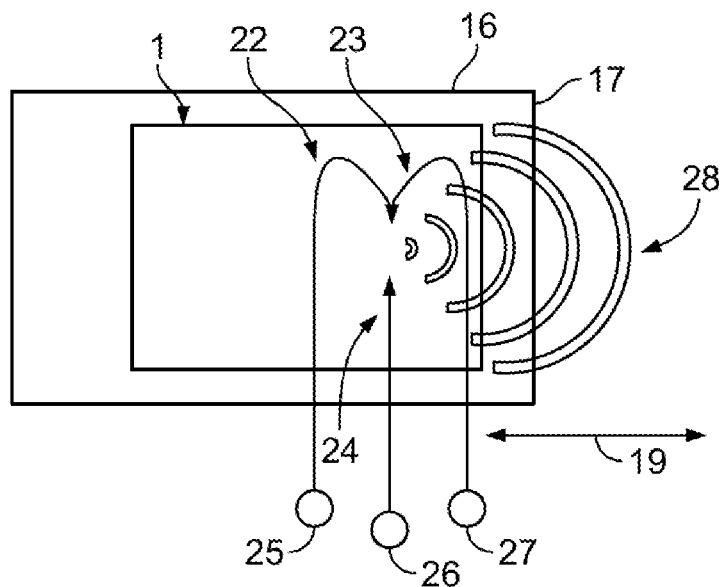
FIG. 3 is a simplified depiction of an electro-hydraulic pressure pulse/shock wave generator having no reflector or focusing element. Thus, the waves of the generator did not pass through a focusing element prior to exiting it.

FIG. 3 is a simplified depiction of the pressure pulse/shock wave apparatus having no focusing reflector or other focusing element. The generated waves emanate from the apparatus without coming into contact with any focusing elements. FIG. 3 shows, as an example, an electrode as a pressure pulse generating element producing divergent waves (28) behind the ignition point defined by a spark between the tips of the electrode (23, 24).

Figure 4A:
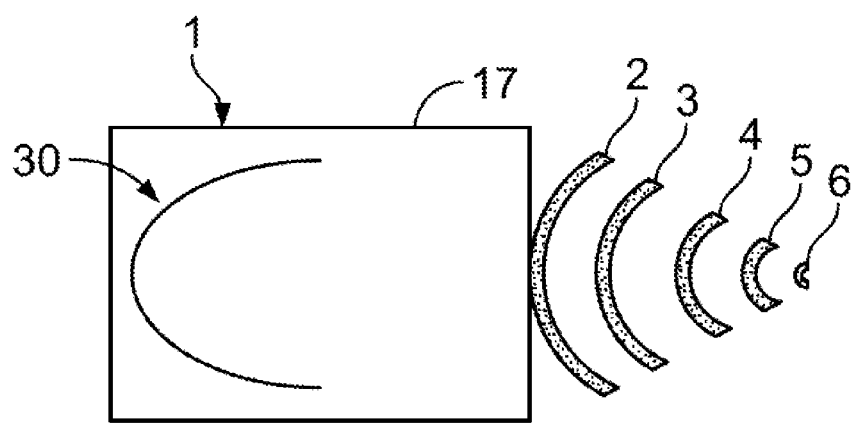
FIG. 4a is a simplified depiction of a pressure pulse/shock wave generator having a focusing element in the form of an ellipsoid. The waves generated are focused.

FIG. 4a is a simplified depiction of the pressure pulse/shock wave generator (shock wave head) having as focusing element an ellipsoid (30). Thus, the generated waves are focused at (6).

Figure 4B:
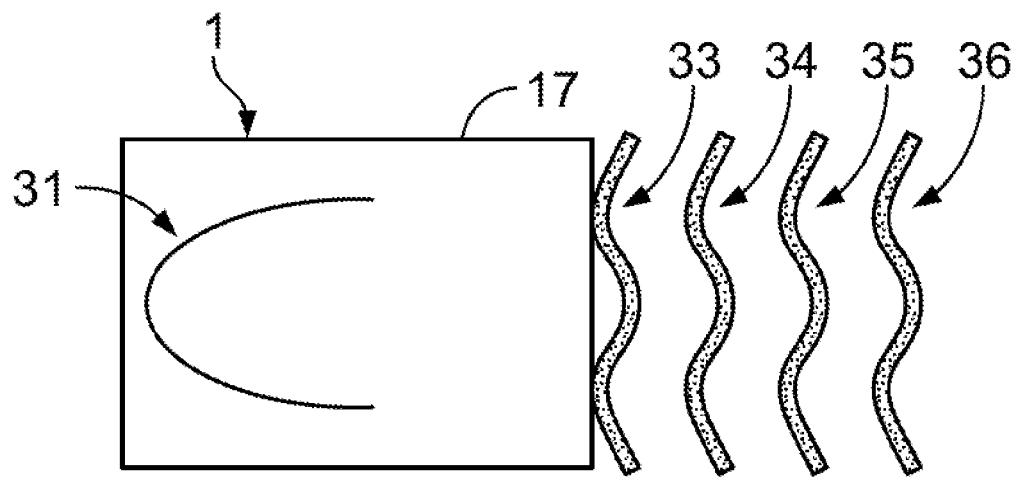
FIG. 4b is a simplified depiction of a pressure pulse/shock wave generator having a parabolic reflector element and generating waves that are disturbed plane.

FIG. 4b is a simplified depiction of the pressure pulse/shock wave generator (shock wave head) having as a focusing element an paraboloid ($y2=2px$). Thus, the characteristics of the wave fronts generated behind the exit window (33, 34, 35, and 36) are disturbed plane ("parallel"), the disturbance resulting from phenomena ranging from electrode burn down, spark ignition spatial variation to diffraction effects. However, other phenomena might contribute to the disturbance.

Figure 4C:
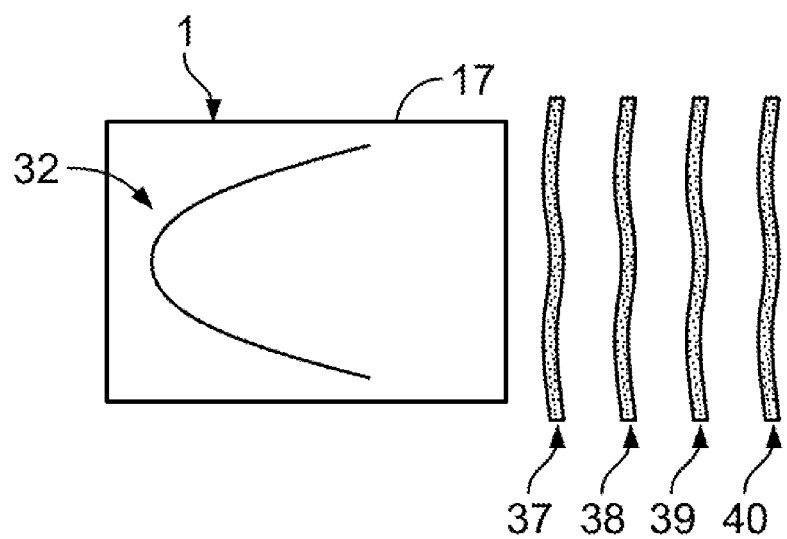
FIG. 4c is a simplified depiction of a pressure pulse/shock wave generator having a quasi parabolic reflector element (generalized paraboloid) and generating waves that are nearly plane/have nearly plane characteristics.

FIG. 4c is a simplified depiction of the pressure pulse/shock wave generator (shock wave head) having as a focusing element a generalized paraboloid ($yn=2px$, with $1.2<n<2.8$ and $n\neq 2$). Thus, the characteristics of the wave fronts generated behind the exit window (37, 38, 39, and 40) are, compared to the wave fronts generated by a paraboloid ($y2=2px$), less disturbed, that is, nearly plane (or nearly parallel or nearly even (37, 38, 39, 40)). Thus, conformational adjustments of a regular paraboloid ($y2=2px$) to produce a generalized paraboloid can compensate for disturbances from, e.g., electrode burn down. Thus, in a generalized paraboloid, the characteristics of the wave front may be nearly plane due to its ability to compensate for phenomena including, but not limited to, burn down of the tips of the electrode and/or for disturbances caused by diffraction at the aperture of the paraboloid. For example, in a regular paraboloid ($y2=2px$) with p=1.25, introduction of a new electrode may result in p being about 1.05. If an electrode is used that adjusts itself to maintain the distance between the electrode tips ("adjustable electrode") and assuming that the electrodes burn down is 4 mm (z=4 mm), p will increase to about 1.45. To compensate for this burn down, and here the change of p, and to generate nearly plane wave fronts over the life span of an electrode, a generalized paraboloid having, for example n=1.66 or n=2.5 may be used. An adjustable electrode is, for example, disclosed in U.S. Pat. No. 6,217,531.

Figure 4D:
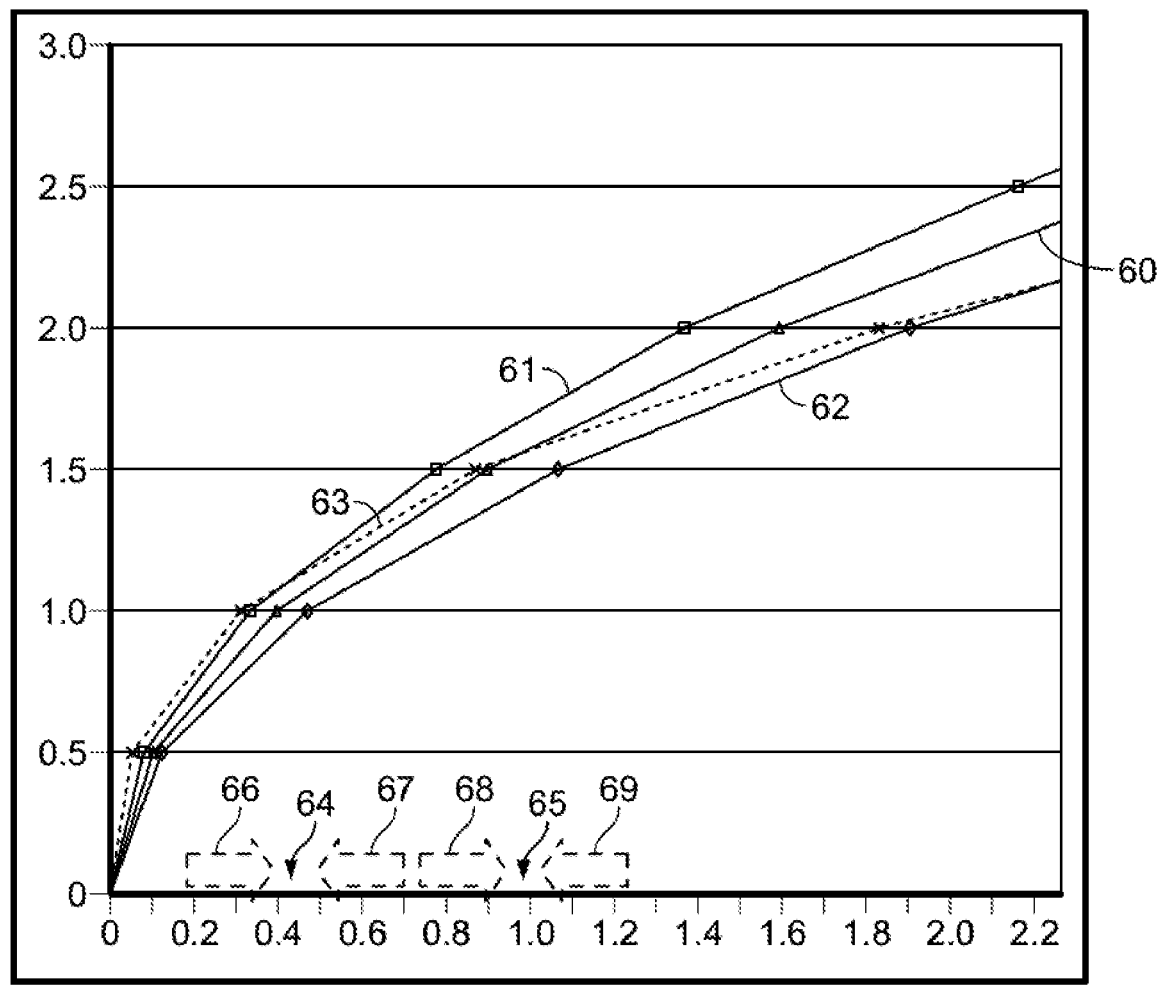
FIG. 4d is a simplified depiction of a generalized paraboloid with better focusing characteristic than a paraboloid in which n=2. The electrode usage is shown. The generalized paraboloid, which is an interpolation (optimization) between two optimized paraboloids for a new electrode and for a used (burned down) electrode is also shown.

FIG. 4d shows sectional views of a number of paraboloids. Numeral 62 indicates a paraboloid of the shape $y2=2px$ with p=0.9 as indicated by numeral 64 at the x axis which specifies the p/2 value (focal point of the paraboloid). Two electrode tips of a new electrode 66 (inner tip) and 67 (outer tip) are also shown in the Figure. If the electrodes are fired and the tips are burning down the position of the tips change, for example, to position 68 and 69 when using an electrode which adjusts its position to compensate for the tip burn down. In order to generate pressure pulse/shock waves having nearly plane characteristics, the paraboloid has to be corrected in its p value. The p value for the burned down electrode is indicate by 65 as p/2=1. This value, which constitutes a slight exaggeration, was chosen to allow for an easier interpretation of the Figure. The corresponding paraboloid has the shape indicated by 61, which is wider than paraboloid 62 because the value of p is increased. An average paraboloid is indicated by numeral 60 in which p=1.25 cm. A generalized paraboloid is indicated by dashed line 63 and constitutes a paraboloid having a shape between paraboloids 61 and 62. This particular generalized paraboloid was generated by choosing a value of $n\neq 2$ and a p value of about 1.55 cm. The generalized paraboloid compensates for different p values that result from the electrode burn down and/or adjustment of the electrode tips.

Figure 5:
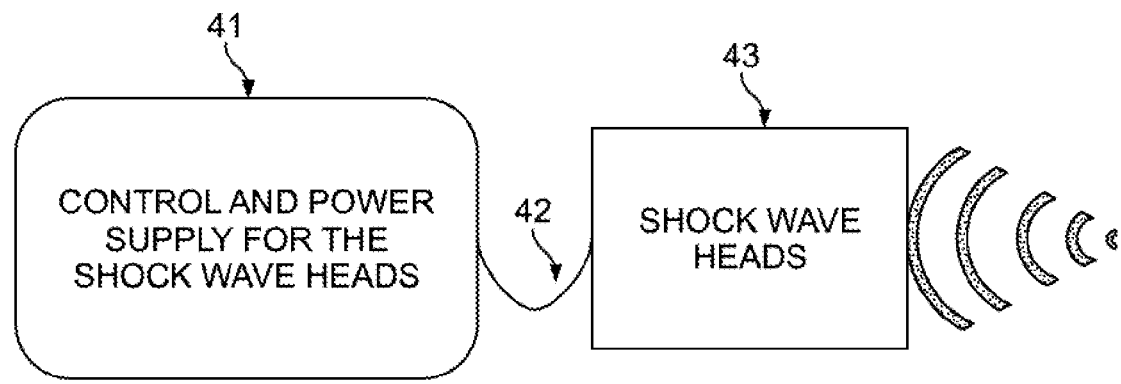
FIG. 5 is a simplified depiction of a pressure pulse/shock wave generator being connected to a control/power supply unit.

FIG. 5 is a simplified depiction of a set-up of the pressure pulse/shock wave generator (43) (shock wave head) and a control and power supply unit (41) for the shock wave head (43) connected via electrical cables (42) which may also include water hoses that can be used in the context of the present invention. However, as the person skilled in the art will appreciate, other set-ups are possible and within the scope of the present invention.

Figure 6:
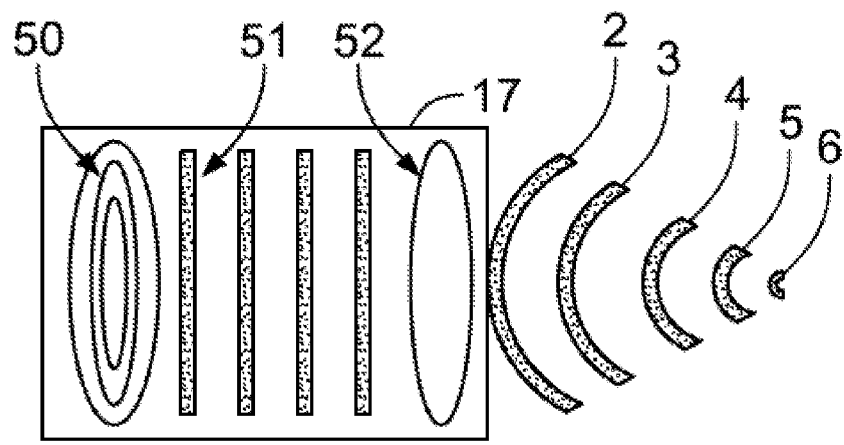
FIG. 6 is a simplified depiction of a pressure pulse/shock wave generator comprising a flat EMSE (electromagnetic shock wave emitter) coil system to generate nearly plane waves as well as an acoustic lens. Convergent wave fronts are leaving the housing via an exit window.

FIG. 6 is a simplified depiction of the pressure pulse/shock wave generator (shock wave head) having an electromagnetic flat coil 50 as the generating element. Because of the plane surface of the accelerated metal membrane of this pressure pulse/shock wave generating element, it emits nearly plane waves which are indicated by lines 51. In shock wave heads, an acoustic lens 52 is generally used to focus these waves. The shape of the lens might vary according to the sound velocity of the material it is made of. At the exit window 17 the focused waves emanate from the housing and converge towards focal point 6.

Figure 7:
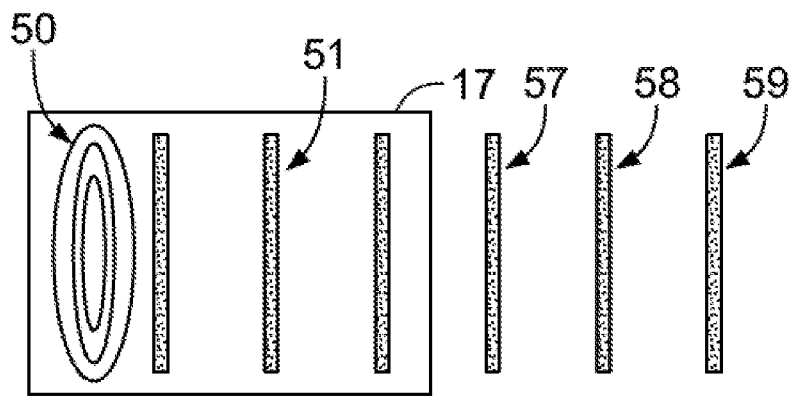
FIG. 7 is a simplified depiction of a pressure pulse/shock wave generator having a flat EMSE coil system to generate nearly plane waves. The generator has no reflecting or focusing element. As a result, the pressure pulse/shock waves are leaving the housing via the exit window unfocused having nearly plane wave characteristics.

FIG. 7 is a simplified depiction of the pressure pulse/shock wave generator (shock wave head) having an electromagnetic flat coil 50 as the generating element. Because of the plane surface of the accelerated metal membrane of this generating element, it emits nearly plane waves which are indicated by lines 51. No focusing lens or reflecting lens is used to modify the characteristics of the wave fronts of these waves, thus nearly plane waves having nearly plane characteristics are leaving the housing at exit window 17.

Figure 8:
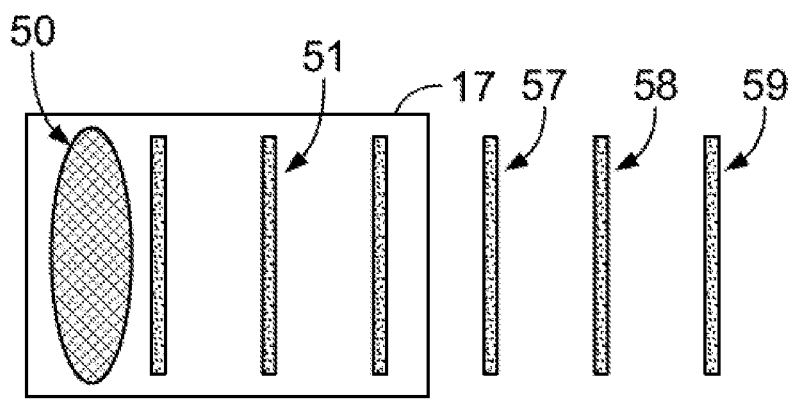
FIG. 8 is a simplified depiction of a pressure pulse/shock wave generator having a flat piezoceramic plate equipped with a single or numerous individual piezoceramic elements to generate plane waves without a reflecting or focusing element. As a result, the pressure pulse/shock waves are leaving the housing via the exit window unfocused having nearly plane wave characteristics.

FIG. 8 is a simplified depiction of the pressure pulse/shock wave generator (shock wave head) having a piezoceramic flat surface with piezo crystals 55 as the generating element. Because of the plane surface of this generating element, it emits nearly plane waves which are indicated by lines 51. No focusing lens or reflecting lens is used to modify the characteristics of the wave fronts of these waves, thus nearly plane waves are leaving the housing at exit window 17. Emitting surfaces having other shapes might be used, in particular curved emitting surfaces such as those shown in FIGS. 4a to 4c as well as spherical surfaces. To generate waves having nearly plane or divergent characteristics, additional reflecting elements or lenses might be used. The crystals might, alternatively, be stimulated via an electronic control circuit at different times, so that waves having plane or divergent wave characteristics can be formed even without additional reflecting elements or lenses.

Figure 9:
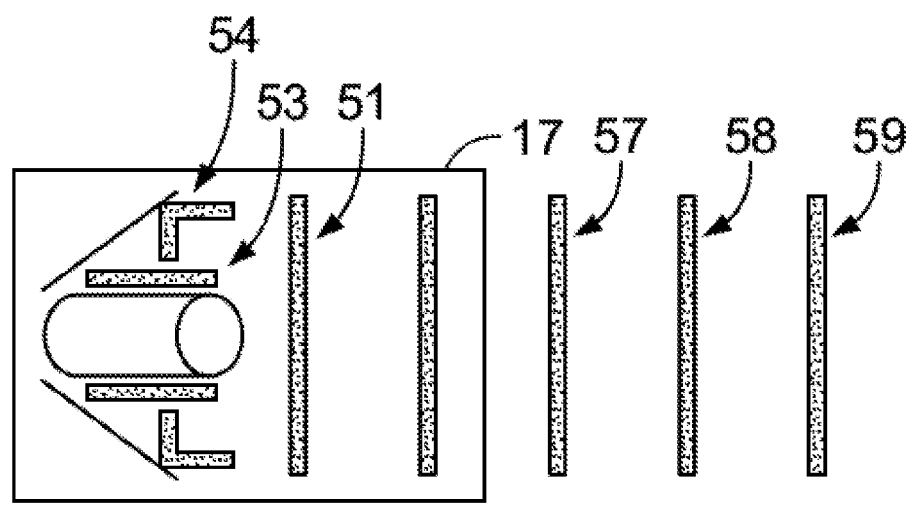
FIG. 9 is a simplified depiction of a pressure pulse/shock wave generator having a cylindrical EMSE system and a triangular shaped reflecting element to generate plane waves. As a result, the pressure pulse/shock waves are leaving the housing via the exit window unfocused having nearly plane wave characteristics.

FIG. 9 is a simplified depiction of the pressure pulse/shock wave generator (shock wave head) comprising a cylindrical electromagnet as a generating element 53 and a first reflector having a triangular shape to generate nearly plane waves 54 and 51. Other shapes of the reflector or additional lenses might be used to generate divergent waves as well.

Figure 10:
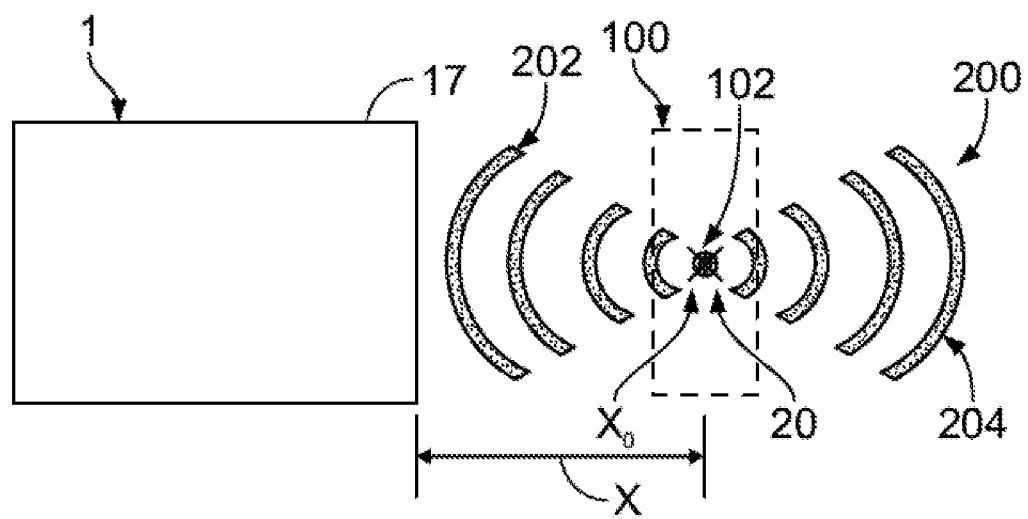
FIG. 10 is a simplified depiction of a pressure pulse/shock wave (PP/SW) generator with focusing wave characteristics shown focused with the focal point or geometrical focal volume being on an organ, the focus being targeted on the location $X_0$.
Figure 11:
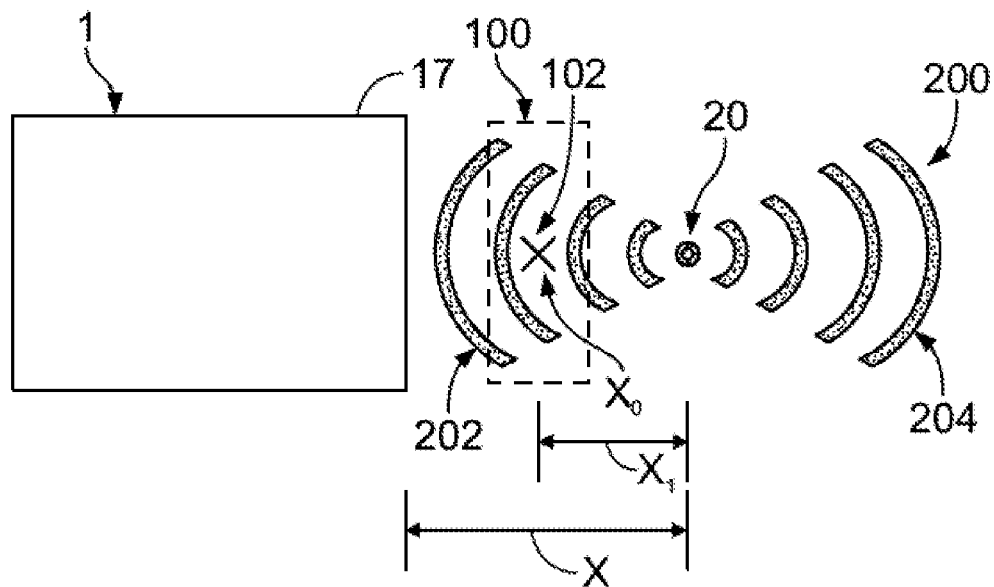
FIG. 11 is a simplified depiction of a pressure pulse/shock wave (PP/SW) generator with the focusing wave characteristics shown wherein the focus is located a distance $X_1$ from the location $X_0$ of an organ wherein the converging waves impinge the organ.
Figure 12:
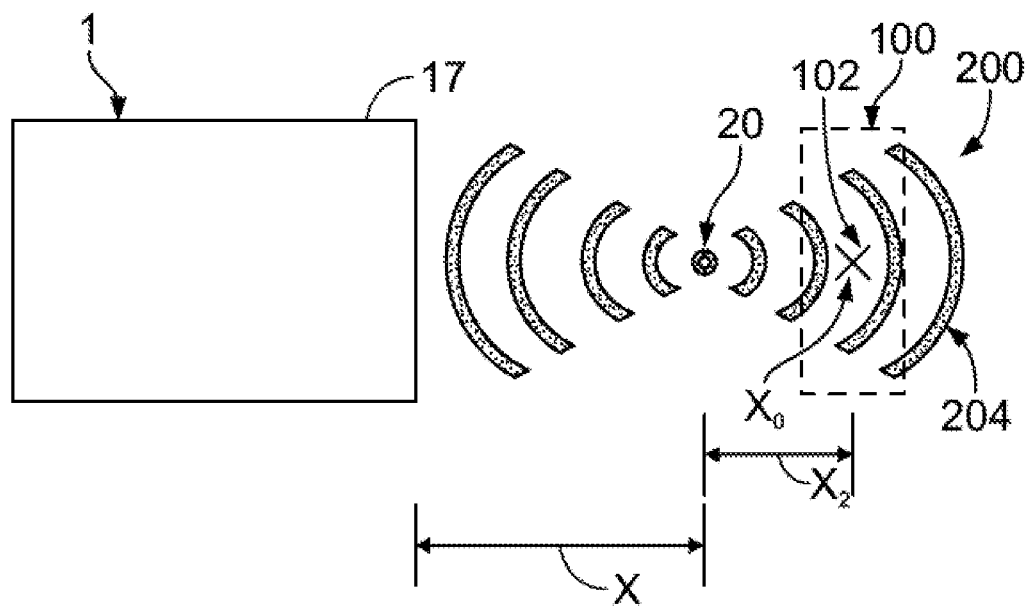
FIG. 12 is a simplified depiction of a pressure pulse/shock wave (PP/SW) generator with focusing wave characteristics shown wherein the focus is located a distance $X_2$ from the mass location $X_0$ wherein the emitted divergent waves impinge the organ.

With reference to FIGS. 10, 11 and 12 a schematic view of a shock wave generator or source 1 is shown emitting a shock wave front 200 from an exit window 17. These FIGS. 10, 11 and 12 are particularly directed to destroying a mass like a tumor and provide a good example of how a focused wave could be used as an option to the unfocused wave if used at a low energy for fat grafting. The shock wave front 200 has converging waves 202 extending to a focal point or focal geometric volume 20 at a location spaced a distance X from the generator or source 1. Thereafter the wave front 200 passes from the focal point or geometric volume 20 in a diverging wave pattern as has been discussed in the various other FIGS. 1-9 generally.

With particular reference to FIG. 10 a tissue 100 is shown generally centered on the focal point or volume 20 at a location $X_0$ within the tissue 100. In this orientation the emitted waves are focused and thus are emitting a high intensity acoustic energy at the location $X_0$. This location $X_0$ can be anywhere within or on the organ. Assuming the tissue 100 is a brain tissue having a tumorous mass 102 at location $X_0$ then the focus is located directly on the mass 102. In one method of treating an infection or mass 102 these focused waves can be directed to destroy or otherwise reduce the mass 102 by weakening the outer barrier shield of the mass 102.

With reference to FIG. 11, the tissue 100 is shifted a distance X toward the generator or source 1. The tissue 100 at location $X_0$ being positioned a distance $X-X_1$ from the source 1. This insures the tissue 100 is impinged by converging waves 202 but removed from the focal point 20. When the tissue 100 is tissue this bombardment of converging waves 202 stimulates the cells activating the desired healing response as previously discussed.

With reference to FIG. 12, the tissue 100 is shown shifted or located in the diverging wave portion 204 of the wave front 200. As shown $X_0$ is now at a distance $X_2$ from the focal point or geometric volume 20 located at a distance X from the source 1. Accordingly $X_0$ is located a distance $X+X_2$ from the source 1. As in FIG. 10 this region of diverging waves 204 can be used to stimulate the tissue 100 which when the tissue is a cellular tissue stimulates the cells to produce the desired healing effect or response. With this acoustic wave background the reader's attention is directed to the inventive applications for fat tissue grafting.

Figure 13:
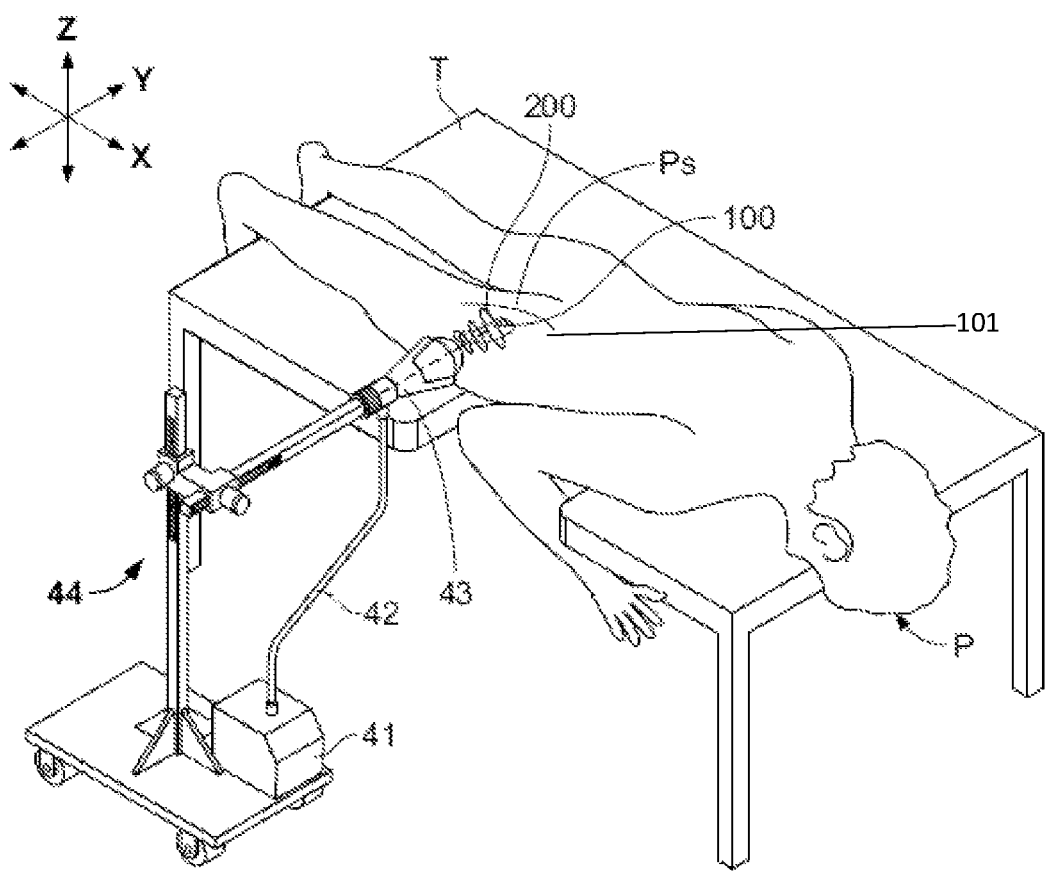
FIG. 13 shows a patient being treated extracorporeally with shock waves being transmitted through the skin to the region of the buttocks to be treated.

With reference to FIG. 13, a perspective view of a portion of a treatment site 200 is shown below the lower back in the buttocks. The soft tissue 100 in the buttocks 101 includes muscle and fat cells and vascular tissue with blood vessels. With further reference to FIG. 13, the patient P who is desiring to improve the appearance and shape of the buttocks is positioned on a table T preferably face down lying on the stomach. A shock wave applicator head 43 is brought into contact with the skin $P_s$ preferably an acoustic gel is used to enhance the transmission of the shock waves 200 through the buttocks 101 down to the subsurface tissue 100. The shock wave applicator head 43 is connected via cabling 42 to a power generating unit 41 as shown. The shock wave applicator head 43 can be attached rigidly to a fixture or stand 44 as illustrated or alternatively can be hand held and manipulated across the skin of the buttocks $P_s$ to drive the shock waves 200 in the direction the shock wave head 43 is pointed to activate a stimulating response.

This application of acoustic shock waves when used as a pre-treatment therapy that can be done one or more times to make the buttocks tissue receptive for receiving a fat graft after such treatment. The shock wave pre-treatment conditioning treatment protocol preferably is initially conducted several weeks before the actual fat grafting procedure. The acoustic shock waves, when transmitted across the entire buttocks region, activate a cellular response within the treatment site. This response or stimulation causes an increase of nitric oxide and a release of a variety of growth factors such as VEGF. Alternatively, this step of conditioning the buttocks region or for that matter any site to receive a fat graft can be cone as part of the at grafting either immediately prior to or after or during the procedure. Additionally, due to the low energy levels employed, the conditioning treatments can occur after a period of time after the fat grafting procedure. This conditioning of the soft tissue region or site greatly improves fat cell survivability of a later fat graft procedure. Ideally, the conditioning either before or after a fat grafting procedure is done more than one time, preferably multiple times to endure the best results and a lasting outcome for the patient.

Figure 14:
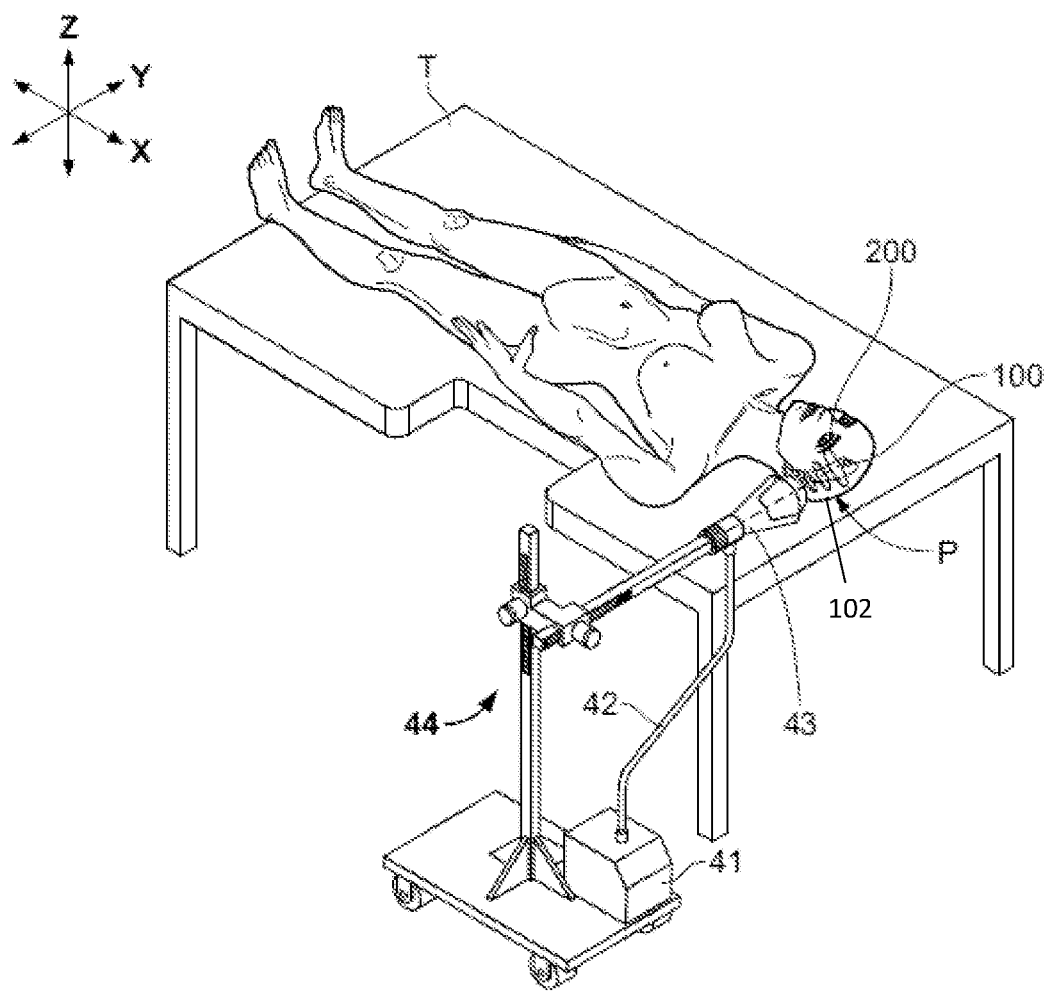
FIG. 14 shows a patient being treated extracorporeally with shock waves being transmitted through the skin to the scalp region to be treated.

In FIG. 14, a patient's P head with the scalp area 102 shown is being conditioned using an acoustic shock wave treatment. In the case of "baldness", the loss of one's hair follicles and the failure to stimulate new growth of follicles has been associated with a lack of viable fat cells and lack of adequate blood flow around the scalp. Early on, the inventors of low energy acoustic shock waves discovered some modest success in causing new hair growth where some underlying hair follicles still survived. This finding was encouraging, but was not particularly useful in the regions devoid of active hair follicles. The present invention has found conditioning the scalp with acoustic shock waves 200 prior to fat grafting the scalp region 102 of baldness enhances the scalp making more receptive to hair transplant procedures by stimulating the underlying tissue by reactivation of dormant hair follicles when encapsulated in a bed of viable fat cells or enriching the transplanted hair plugs in the enriched bed of fat cells in the acoustically treated scalp region. Accordingly, once the fat graft procedure is accomplished additional acoustic shock wave treatments of the hair follicles involved by the viable fat cells underlying the scalp results in a big improvement in hair loss recovery and new hair growth previously bald areas 102 of the scalp. it is believed the combination of conditioning of the scalp prior to and after fat cell grafting is directly responsible for this improved result.

Figure 15:
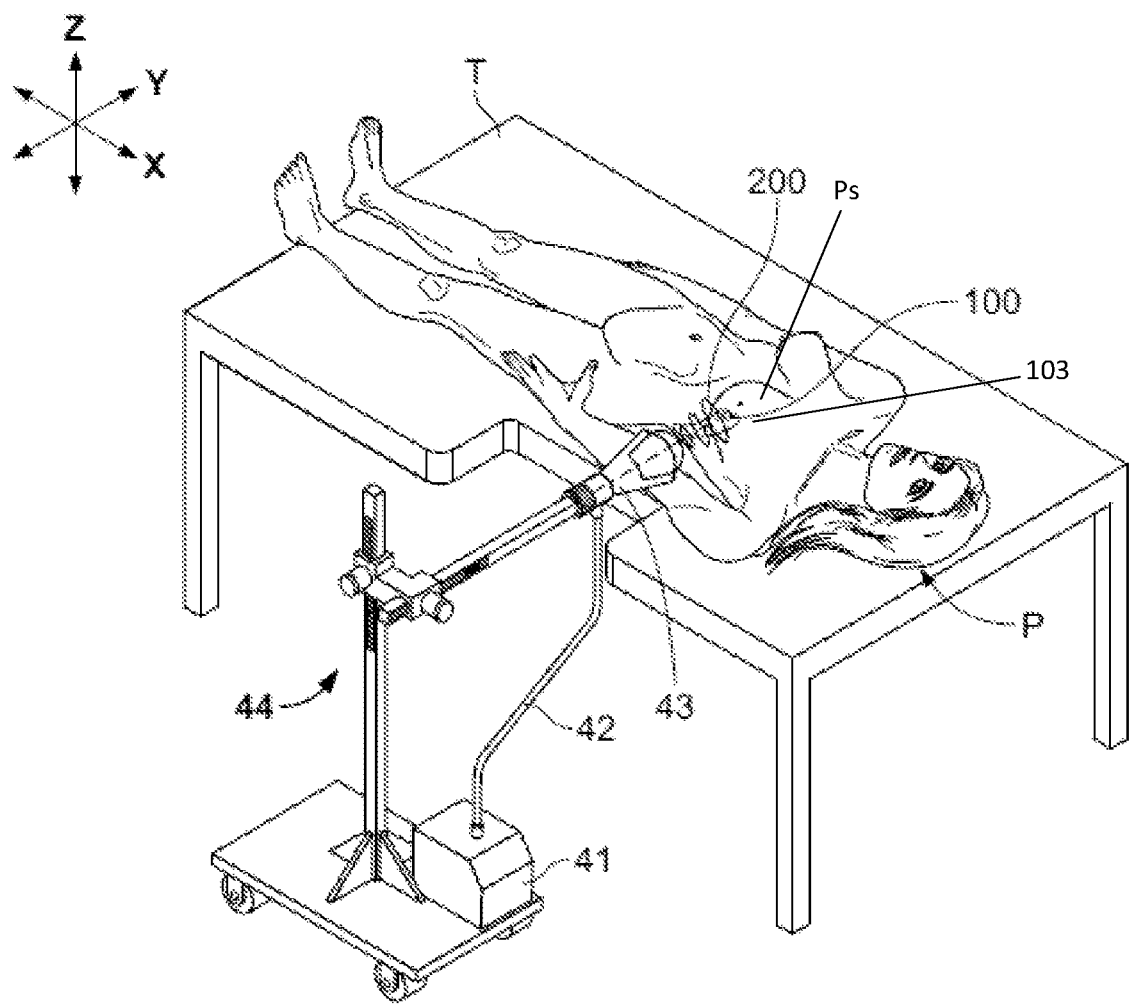
FIG. 15 shows a patient being treated extracorporeally with shock waves being transmitted through the skin to the breast region to be treated.

With reference to FIG. 15, the conditioning with an acoustic shock wave treatment of a soft tissue 100 region of a breast 103 is illustrated. As in the case of the buttocks, the breast is preferably coupled acoustically to a shock wave generator or head 43 using a coating of a coupling gel or liquid to enhance the transmission of the shock waves 200 through the skin $P_s$ to the underlying breast tissue 103. The transmission of the shock waves 200 is preferred of a low energy density of 0.2 mJ/mm$^2$ whether using focused or unfocused shock waves. The acoustic shock waves pulse rapidly through the cells in the breast tissue 103 penetrating the cell membrane extremely rapidly due to the rapid rise to peak time and pass through exiting slower due to the slower return from peak amplitude. This asymmetric wave pattern rapidly compresses each cell on entry and slow decompresses the cell as it exits. This effective squeezing of each cell is believed to cause the release of growth factors such as VEGF and others and also creates nitric oxide, all beneficial to new blood vessel formation. This occurs as a transmission across the cell membranes without rupturing the native cells. This conditioning of the breast tissue using the sonic waves of ultrasonic, or preferably, acoustic shock waves can occur as a conditioning step prior to fat grafting or a step as part of a fat grafting procedure or can occur after the fat grafting procedure or any combination of two or more of these. The step of conditioning prior to or after a fat grafting procedure, preferably involves multiple conditioning treatments or a period of several weeks or months. Post grafting conditioning can occur multiple times over a 6-month period to ensure the most successful fat cell augmentation results. This phenomenon is a unique attribute of low energy or soft wave acoustic shock waves. The end result is an enhanced breast tissue receptive to receiving a fat tissue graft with viable fat cells at an extremely high survival percentage, much higher than achievable without the benefit of the acoustic shock wave pre-conditioning, conditioning or post conditioning or combinations of these. As previously noted, the survival rate of fat cell grafts ranges from 50 to 90 percent. With the present invention, the survival rate is improved to 90 to up to 100 percent. This alone makes the use of "fat grafting" for breast augmentation a preferred treatment because the augmented breast is 100 percent natural and all achieved using the patient's own fat cells.

Figure 16:
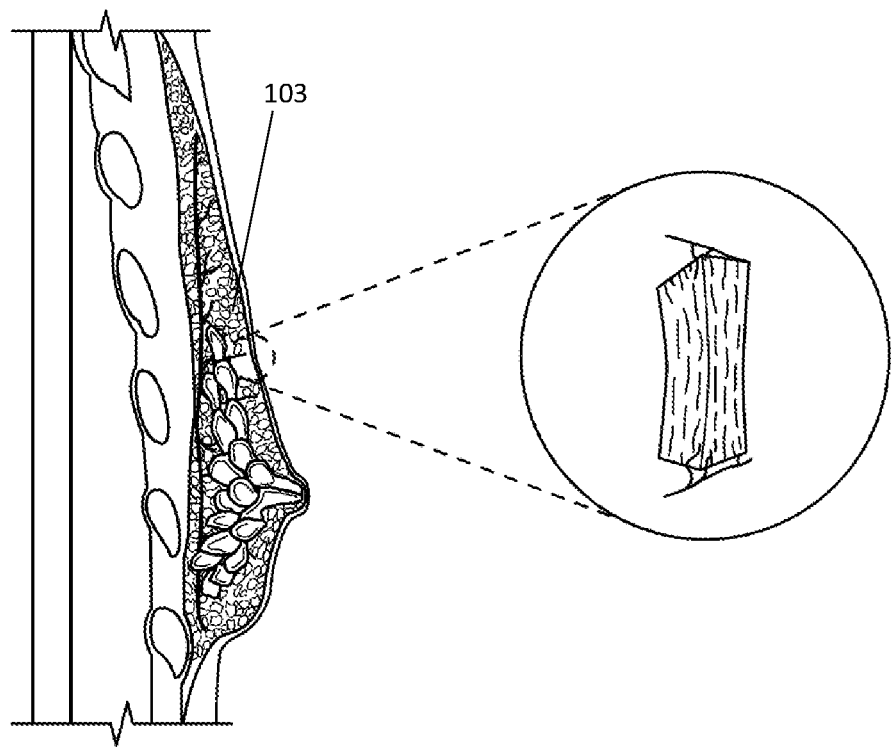
FIG. 16 shows breast tissue before being prepared to be injected with fat cells.
Figure 17:
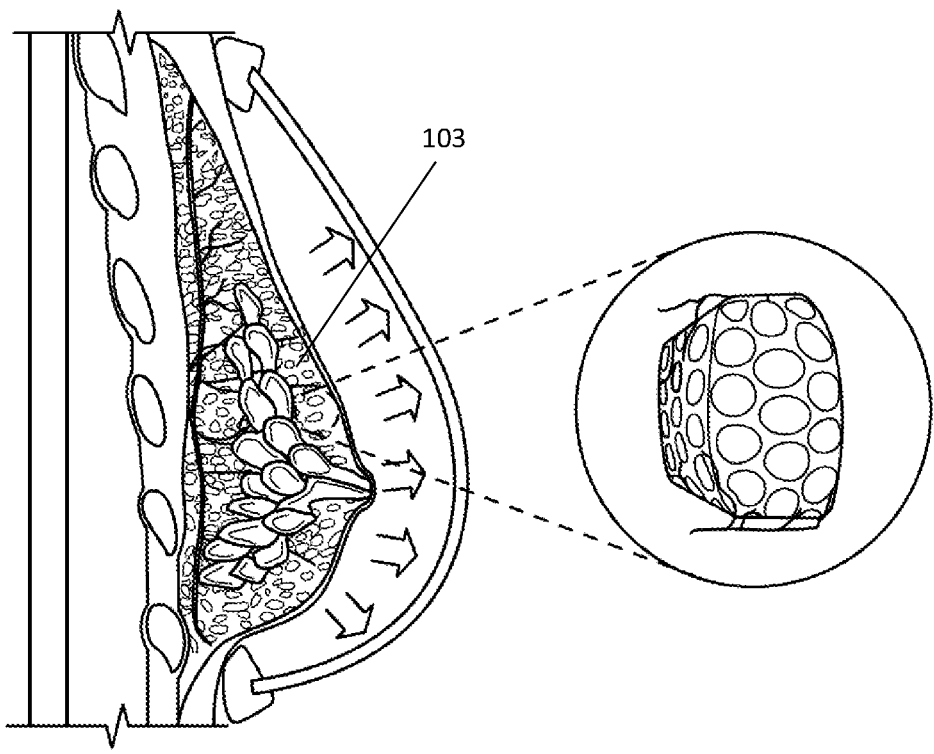
FIG. 17 shows breast tissue being prepared to be injected with fat cells.
Figure 18:
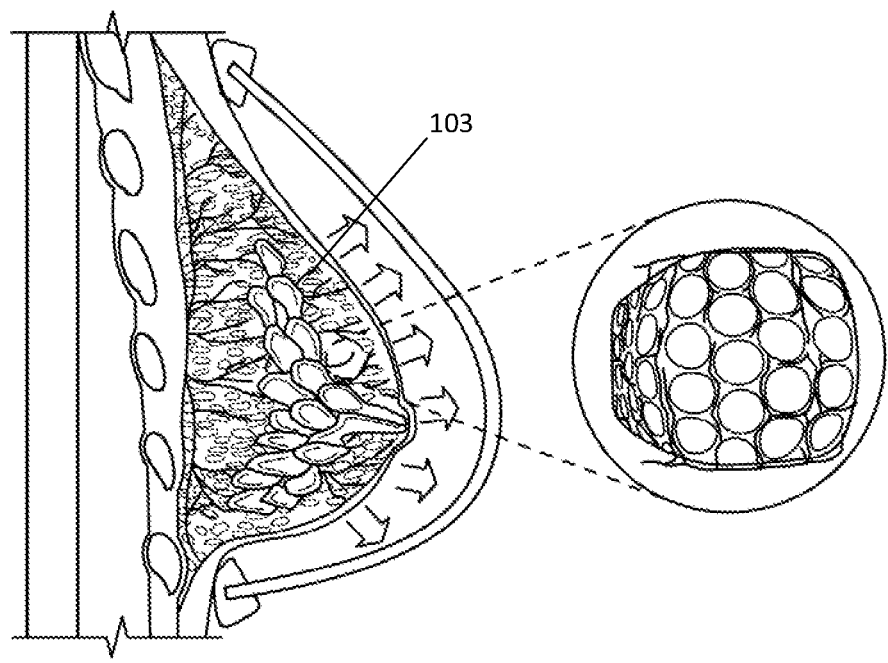
FIG. 18 shows breast tissue ready to be injected with fat cells.
Figure 19:
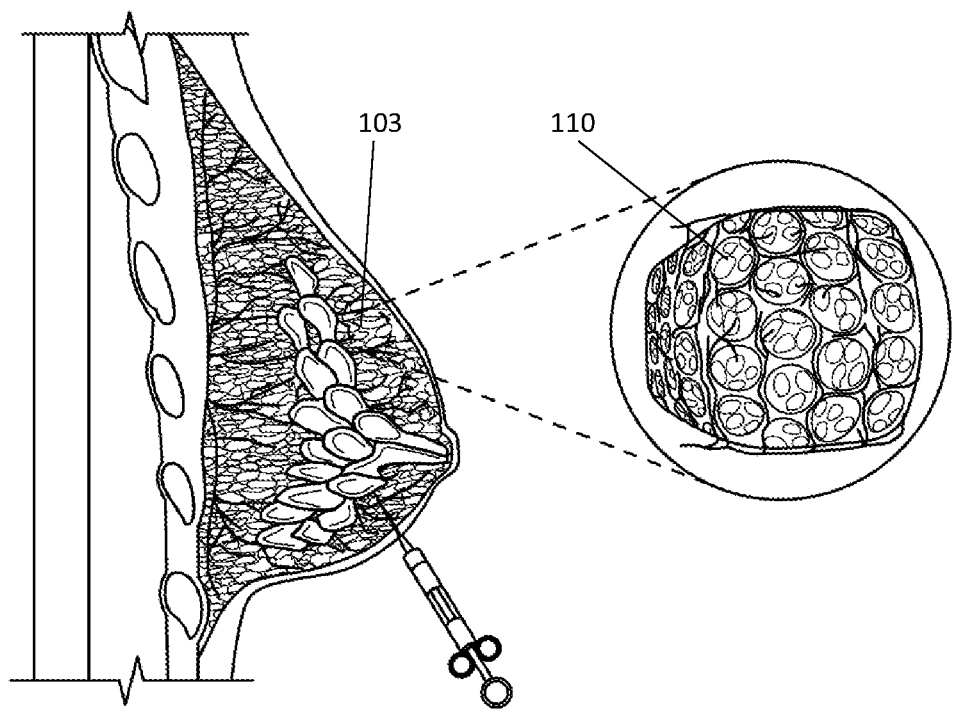
FIG. 19 shows breast tissue being injected with fat cells.

FIGS. 16-19 illustrate an alternative treatment for breasts that can be used in combination with the present invention and show breast tissue 103 in various stages of augmentation. FIG. 16 shows original small breast before treatment. The inset shows normal tissue density. FIG. 17 illustrates an example of the use of a vacuum system called BRAVA used by Dr. Khouri to improve fat cell viability with a focus on mechanically loosening the underlying breast tissue. The BRAVA system is placed over the breast area when the patient sleeps. Vacuum inside the domes pulls the breast tissue 103 outward to start expansion. The inset shows loosening of the normal tissue density which is the key for a high rate of fat survival. FIG. 18 illustrates continued expansion; the breast enlarges even more. The inset shows the loosening up of the tissues as they open up like an expanding sponge to make room for the grafts. Notice that with this rapid expansion there aren't any new fat cells, only a loosening of the normal tissue density with stretched out fibers and tiny new blood capillaries along the expanded structure ready to accept the grafts. In FIG. 19, the expanded space is grafted with fat 110 harvested from the patient's desired body area. No cuts or incisions are made, only needle pokes. The fat 110 fills up the expanded vascular structure and restores the normal cellular density. The inset shows how new blood vessels help keep the fat deposits alive. The breast has been augmented with tissue engineered fat 110.

Furthermore, such acoustic shock wave forms can be used in combination with drugs, chemical treatments, irradiation therapy or even physical therapy and when so combined the stimulated cells will more rapidly assist the body's natural healing response and thus overcomes the otherwise potentially tissue damaging effects of these complimentary procedures.

The present invention provides an apparatus for an effective treatment of indications, which benefit from high or low energy pressure pulse/shock waves having focused or unfocused, nearly plane, convergent or even divergent characteristics. With an unfocused wave having nearly plane, convergent wave characteristic or even divergent wave characteristics, the energy density of the wave may be or may be adjusted to be so low that side effects including pain are very minor or even do not exist at all.

In certain embodiments, the apparatus of the present invention is able to produce waves having energy density values that are below 0.1 mJ/mm$^2$ or even as low as 0.000 001 mJ/mm$^2$. In a preferred embodiment, those low end values range between 0.1-0.001 mJ/mm$^2$. With these low energy densities, side effects are reduced and the dose application is much more uniform. Additionally, the possibility of harming surface tissue is reduced when using an apparatus of the present invention that generates unfocused waves having planar, nearly plane, convergent or divergent characteristics and larger transmission areas compared to apparatuses using a focused shock wave source that need to be moved around to cover the affected area. The apparatus of the present invention also may allow the user to make more precise energy density adjustments than an apparatus generating only focused shock waves, which is generally limited in terms of lowering the energy output. Nevertheless, in some cases the first use of a high energy focused shock wave targeting a treatment zone may be the best approach followed by a transmission of lower energy unfocused wave patterns.

It will be appreciated that the apparatuses and processes of the present invention can have a variety of embodiments, only a few of which are disclosed herein. It will be apparent to the artisan that other embodiments exist and do not depart from the spirit of the invention. Thus, the described embodiments are illustrative and should not be construed as restrictive.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A method of conditioning a soft tissue region or site of a patient prior to a fat grafting procedure or as part of the fat grafting procedure or after a fat grafting procedure, or any combination of conditioning prior to, during or after a fat grafting procedure, comprises the steps of:
    activating sonic waves of either an ultrasonic wave generator or source or an acoustic shock wave generator or source to emit ultrasonic waves or acoustic shock waves;
    subjecting the soft tissue region or site to ultrasonic waves or acoustic shock waves stimulating the said soft tissue;
    implanting or injecting viable fat cells in a fat grafting procedure to the stimulated soft tissue regions; and
    wherein the emitted sonic waves are focused or unfocused low energy acoustic shock waves or ultrasonic waves.

2. The method of conditioning a soft tissue region or site of claim 1 wherein the soft tissue region or site underlies the patient's skin.

3. The method of conditioning a soft tissue region or site of claim 2 wherein the shock wave generator is acoustically coupled to the patient's skin using a coupling gel or liquid.

4. The method of conditioning a soft tissue region or site of claim 1 wherein the soft tissue region or site is one of a buttock, a breast or a scalp.

5. The method of conditioning a soft tissue region or site of claim 1 wherein the conditioning of the soft tissue site causes a release of nitric oxide.

6. The method of conditioning a soft tissue region or site of claim 5 wherein the conditioning of the soft tissue site causes a release of growth factors including, but not limited to VGEF.

7. The method of conditioning a soft tissue region or site of claim 6 wherein the conditioning of the soft tissue causes new blood vessels to be created increasing vascularization.

8. The method of conditioning a soft tissue region or site of claim 1 is repeated one or more times prior to a fat grafting procedure.

9. The method of conditioning a soft tissue region or site of claim 1 wherein the emitted ultrasonic waves or acoustic shock waves are low energy soft waves.

10. The method of conditioning a soft tissue region or site of claim 9 wherein the low energy soft waves have an energy density of 0.2 mJ/mm$^2$.

11. The method of conditioning a soft tissue region or site of claim 1 wherein the soft tissue region or site receives between 2000 and 6000 acoustic shock waves or ultrasonic waves.

12. The method of conditioning a soft tissue region or site of claim 1 further comprises the step of:
    subjecting the soft tissue region or site prior to receiving or after the fat grafting procedure.

13. The method of conditioning a soft tissue region or site of claim 12 further comprises the step of:
    verifying or measure a survival rate of the fat cells after a period of several weeks after the fat graft procedure.

14. The method of conditioning a soft tissue region or site of claim 1 further comprises the step of:
    repeating the step of subjecting the soft tissue region or target site to acoustic shock waves after a period of time after the fat grafting procedure to maintain tissue stimulation.

15. The method of conditioning a soft tissue region or site of claim 4 wherein the tissue region is a scalp and at least a portion of the scalp is a bald region.

16. The method of conditioning a soft tissue region or site of claim 15 wherein the bald region is being conditioned for receiving a hair transplant.

17. The method of conditioning a soft tissue region or site of claim 1 wherein the sonic waves are acoustic shock waves.

18. The method of conditioning a soft tissue region or site of claim 1 where the sonic waves are ultrasonic waves.

* * * * *